United States Patent [19]
Liu

[11] Patent Number: 5,859,535
[45] Date of Patent: Jan. 12, 1999

[54] SYSTEM FOR DETERMINING SIZE AND LOCATION OF DEFECTS IN MATERIAL BY USE OF MICROWAVE RADIATION

[75] Inventor: John M. Liu, Columbia, Md.

[73] Assignee: The United States of America as represented by the Secretary of the Navy, Washington, D.C.

[21] Appl. No.: 798,683

[22] Filed: Feb. 12, 1997

[51] Int. Cl.$^6$ .................................................. G01N 22/04
[52] U.S. Cl. ......................... 324/632; 324/642; 324/644; 324/534
[58] Field of Search .................................. 324/642, 644, 324/632, 534

[56] References Cited

U.S. PATENT DOCUMENTS

| | | |
|---|---|---|
| 3,144,601 | 8/1964 | Slabodsky . |
| 3,233,172 | 2/1966 | Luoma . |
| 3,549,986 | 12/1970 | Prine . |
| 3,562,642 | 2/1971 | Hochschild . |
| 3,810,005 | 5/1974 | Bennion et al. . |
| 4,097,796 | 6/1978 | Lunden . |
| 4,255,702 | 3/1981 | Tricoles et al. . |
| 4,344,030 | 8/1982 | Auderson et al. . |
| 4,500,835 | 2/1985 | Heikila .................................... 324/642 |
| 4,514,680 | 4/1985 | Heikkila . |
| 4,707,652 | 11/1987 | Lowitz . |
| 5,068,614 | 11/1991 | Fields et al. . |
| 5,216,372 | 6/1993 | Zoughi et al. . |
| 5,363,050 | 11/1994 | Guo ......................................... 324/642 |
| 5,384,543 | 1/1995 | Bible et al. . |
| 5,440,238 | 8/1995 | Martens ................................... 324/642 |
| 5,497,100 | 3/1996 | Reiser ..................................... 324/642 |
| 5,502,394 | 3/1996 | Piau ........................................ 324/642 |

OTHER PUBLICATIONS

Microwave Remote Sensing of An Internal Air–gap or Void in Dielectric Material by John M. Liu—dated 21 May 1996.

*Primary Examiner*—Josie Ballato
*Assistant Examiner*—Jose M. Solis
*Attorney, Agent, or Firm*—John Forrest; Jacob Shuster

[57] ABSTRACT

Microwave radiation emitted from a single antenna is focused on a targeted material from which reflected radiation is received by the same antenna to provide signal measurement data from which detected material defects are evaluated by determination of void location and size. Antenna position and orientation is adjusted to obtain the signal measurement data from of the microwave radiation reflection along at least two target incidence paths from the same target location, one of which is normal to said targeted surface of the material and the other oblique thereto at a scattering angle at which the signal radiation intensity is minimized.

8 Claims, 4 Drawing Sheets

SYSTEM FOR DETERMINING SIZE AND LOCATION OF DEFECTS IN MATERIAL BY USE OF MICROWAVE RADIATION

The present invention relates generally to non-destructive evaluation of internal defects within non-metallic materials by use of microwave radiation.

BACKGROUND OF THE INVENTION

The detection and evaluation of defects within various non-metallic materials by non-destructive use of radiation is generally known in the art, including use of microwave radiation exhibiting certain advantages over other forms of radiation such as x-ray, ultrasound and thermography radiation. Such prior art use of microwave radiation include emission and back-scattering of the emitted radiation after interaction with the targeted material for detecting the presence or absence of a defect therein. Microwave radiation types of defect detection systems heretofore involved one or more antennas for emission of the radiation and reception of reflective back-scattering thereof. Some of the advantages over the use of other forms of radiation include, avoiding use of a couplant and heat diffusion means, increasing depth of detection and avoiding the provision of radiation hazard prevention. It is therefore an important object of the present invention to enlarge evaluation of defects in non-metallic materials by the advantageous use of microwave radiation.

SUMMARY OF THE INVENTION

In accordance with the present invention, microwave radiation is both emitted from and received by a single antenna that is adjustably positioned and orientated to both transmit and receive microwave energy along each of at least two angularly related target incidence paths intersecting targeted material at a void as a focus location from which the radiation is reflected along such paths for reception by the same antenna, by means of a defect hidden within the material is detected and evaluated as to location and size in terms of by the defect void thickness and its lateral extent based on measurements of microwave radiation. The intensity of such the microwave radiation is measured along one of the angularly related incidence paths normal to the targeted material from which void volume is determined, whereas measurements of minimized intensity along an oblique incidence path at a scattering angle to the normal incidence path is selected to determine the lateral extent of the void. Also, separation in arrival time between radiation from the void and external boundaries of the targeted material enables, determination of void location dependent on the dielectric properties of the targeted material and the frequency bandwidth of the radiation.

The foregoing referred to determinations of both defect location and size is achieved through calculations based on radiation signal measurement data that is digitized and stored in a computer for conversion between frequency domain and time domain through Fourier transformations so as to gate out signal measurement data derived from pulse-echos not associated with the void of interest and to examine isolated void signals one frequency at a time.

BRIEF DESCRIPTION OF DRAWING FIGURES.

A more complete appreciation of the invention and many of its attendant advantages will be readily appreciated as the same becomes better understood by reference to the following detailed description when considered in connection with the accompanying drawing wherein.

DETAILED DESCRIPTION OF PREFERRED EMBODIMENTS

Figure 1:
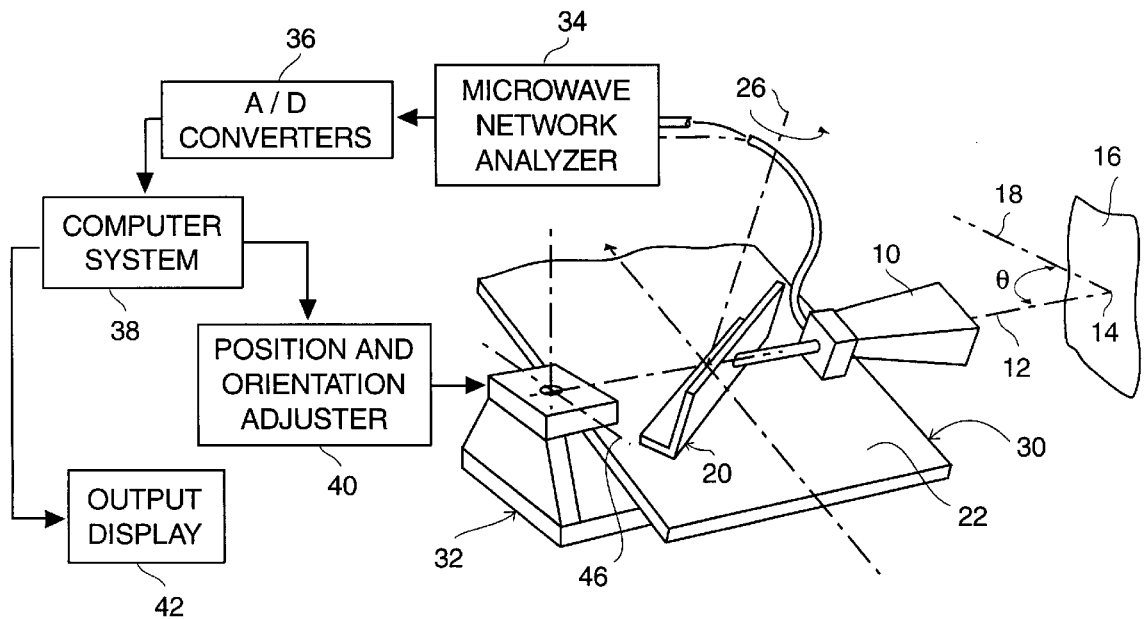
FIG. 1 is a simplified perspective view of an antenna arrangement in accordance with the present invention for emission and reception of microwave radiation focused on targeted material, together with a block diagram of a defect detection and evaluation system associated therewith.

Referring now to the drawing in detail, FIG. 1 depicts a single antenna 10 from which a microwave radiation beam is emitted toward a focus location 14 in a non-metallic target such as dielectric materials or composites. Such outgoing antenna beam is shown directed perpendicular to the targeted surface of dielectric material 16 so as to form a normal incidence path 12 for the microwave radiation which is reflected back along such path to the same antenna 10 from the target surface which is spaced by a stand-off distance from the antenna 10 of at least several inches in accordance with certain embodiments of the present invention. When disposed in another position and at a different angular orientation relative to the target material 16, the antenna 10 emits and receives radiation along an oblique incidence path 18 at a scattering angle ($\theta$) to the normal incidence path 12 as denoted in FIG. 1.

Also depicted by way of example in FIG. 1, is a support arrangement for the antenna 10 so as to accommodate its repositioning and reorientation on a platform 30 for establishment of the two incidence paths 12 and 18. An optical beam splitter 20 shown in FIG. 1 is angularly reoriented about a bearing axis 26 on scattering surface plane 22 of the platform 30, which is supported for angular adjustment about the normal incidence path 12 on a suitable fixed stand 32. As diagrammed in FIG. 2A, the platform 30 also supports an optical mirror 24 which is utilized in cooperation with the beam splitter 20 in a manner generally known in the art to angularly adjust the antenna 10 when repositioned on the platform 30 along a translation path 28 to obtain the oblique incidence path 18 focused on the same target location 14.

FIG. 1 also diagrams an operative connection of the antenna 10 to a calibrated microwave network analyzer 34 which is per se known in the art. Such a microwave network analyzer 34 is marketed for example by the Hewlett-Packard Corporation as model 8722C, and includes a wide frequency band microwave energy source, multi-frequency transmitter and coherent receiver from which signal measurement data is received and coupling circuits through which the transmitter and receiver are operatively connected to the antenna 10 and includes signal separation means for independently processing outgoing and returned scattering signals. Pursuant to the present invention, the processed signal measurement data from the analyzer 34 is digitized by analog-to-digital converters 36 and then fed to and stored within a computer system 38 through which control data is generated and fed to an adjuster 40 for adjustment of position and orientation of the antenna 10 and the scattering plane 22 as aforementioned. Also calculations performed by the computer system with respect to the digitized data from analyzer 34 provides an output display 42 characterizing any detected defects in terms of both location and size.

Figure 2A:
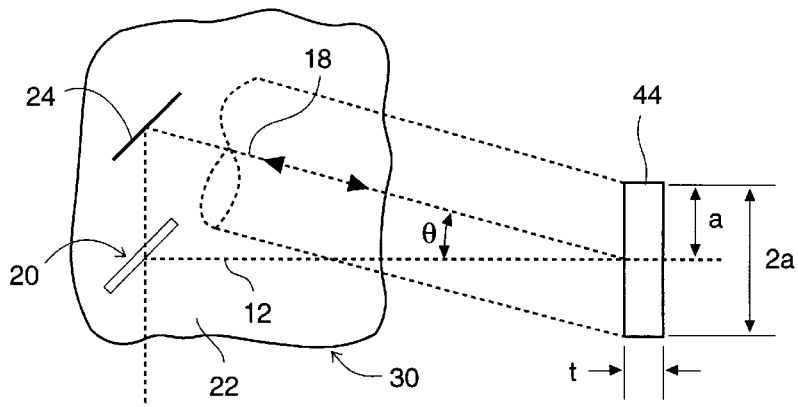
FIGS. 2A and 2B are schematic top and front views depicting certain geometric relationships associated with the arrangement depicted in FIG. 1.
Figure 2B:
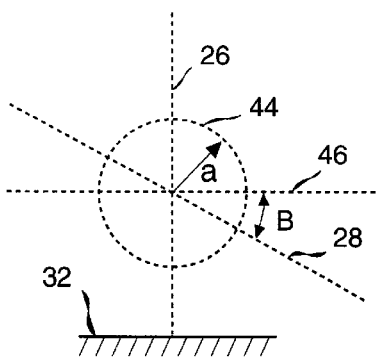

The geometry of the antenna and scattering plane arrangement corresponding to that of FIG. 1 is shown in FIGS. 2A and 2B with respect to a disc-shaped void 44 at the focus location 14 in the material 16 as the detected defect void that has a thickness (t) and a lateral extent in terms of a radius (a). As diagrammed in FIG. 2A, the scattering plane 22 corresponding to paths 12 and 18 is depicted for both the position of the antenna 10 focussed along the normal incidence path 12, and the other oblique incidence position to which it is displaced along the translation path 28. The front view of FIG. 2B shows the antenna 10 positioned on the scattering plane 22 at an azimuthal angle ($\beta$) to horizontal axis 46. Based on the arrangement depicted in FIGS. 1, 2A and 2B, measurements of microwave intensity or signal amplitude (A) is utilized to determine location and size of defects in material 16 as a void having a thickness (t) and a lateral extent in terms of a radius (a).

Figure 3:
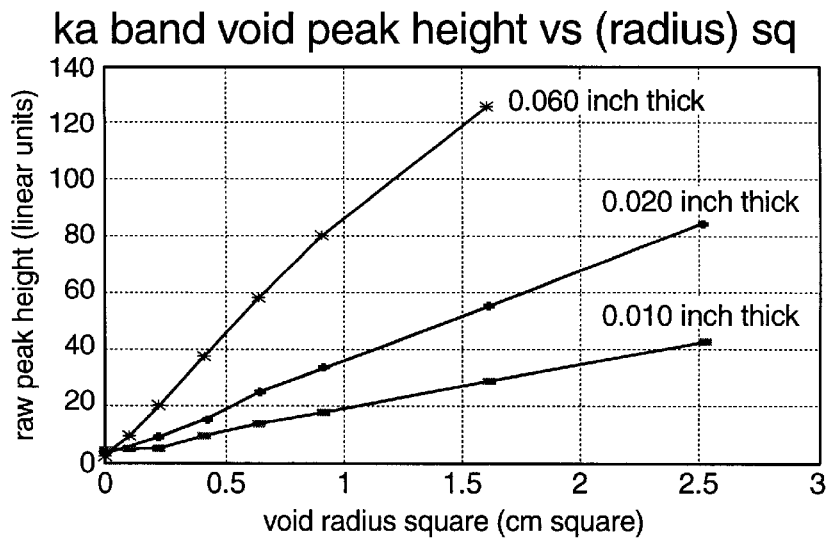
FIGS. 3, 4 and 5 are graphs showing experimental signal measurement data obtained in connection with the present invention.
Figure 4:
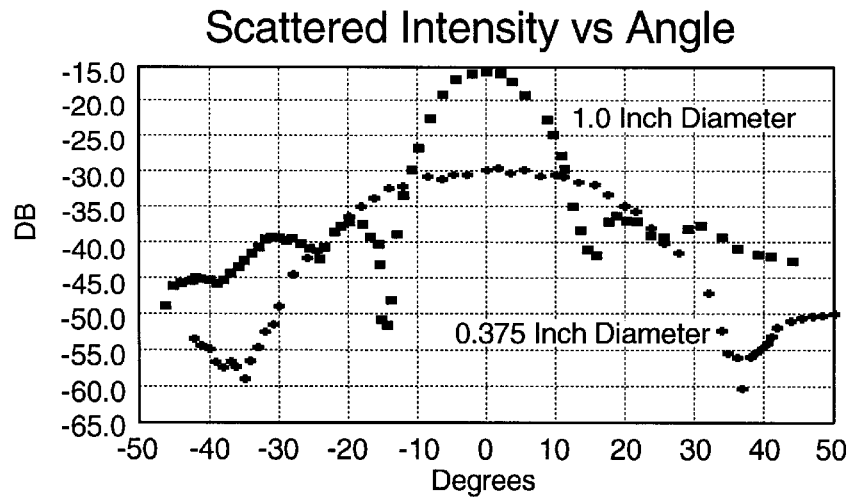

Calculations of defect location and size from measurements of microwave intensity or reflectometer signal amplitude (A), is based on a generally known formula:

$$A = ka^2 F(k,t,e) J_1(2ka \sin \theta)/ka \sin \theta,$$

where F(t,e) is a function of void thickness (t), (e) is the dielectric constant of material 16, (k) is the microwave number $2\pi/\lambda$, $\lambda$ is the wavelength of the microwave radiation, J1 is the Bessel function and ($\theta$) is the scattering angle of the oblique beam path 18. With the antenna 10 in a normal incidence position corresponding to that of path 12 shown in FIG. 2A, the scattering angle ($\theta$) is zero, thereby reducing the latter formula to: $A = ka^2 t$ after normalization for a given material with a fixed value of e. Experimental measurements of the signal amplitude (A) is graphically represented for different void radii (a) in FIG. 3. Such graphical data conforms to the latter formula for signal amplitude (A) along the normal incidence path 12. Such data conforms to the latter mentioned formula predicting the linear relationship of (A) to the scattering volume determined from amplitude measurements with the antenna 10 in the normal incidence position as graphically depicted in FIG. 3. FIG. 4 graphically depicts the variation in signal amplitude (A) for different oblique scattering angles ($\theta$) from recorded experimental measurements of voids having radii of 0.5 inch and 0.1875 inch. As predicted by the first mentioned formula, the signal amplitude (A) decreased as the scattering angle ($\theta$) increased and reached a minimum value away from the normal incidence path on either side thereof. Such minima angles as graphically recorded in FIG. 4 depends on the radius of the void. Thus, for a radius of 1 inch the minima angle is 15° while the minima angle is 35° for a radius of 0.1875 inches. The lateral extent of defect voids on the other hand are calculated from amplitude measurements obtained with the antenna 10 in the oblique incidence positions to determine opening thickness and the lateral radial dimension of the voids.

Figure 5:
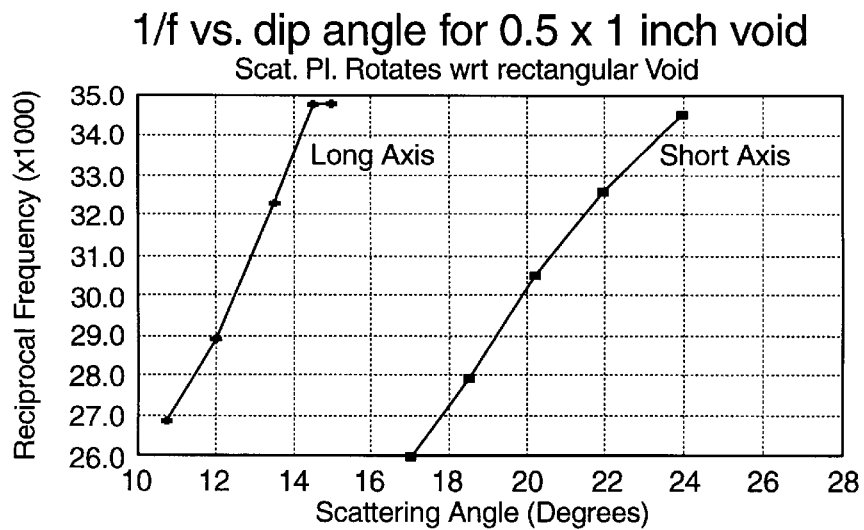

Also pursuant to the present invention, the oblique angle ($\theta$) is selected so that the range of defect sizes to be detected is compatible with available frequencies associated with the microwave source in the analyzer network 34. For frequencies in the range of 8 to 94 GHz angles ($\theta$) of less than 20° are adequate for sizing defects larger than ¼ inch in diameter. Further, experimental data confirms that the correctness in sizing of the defect void is maximized by signal measurement through the antenna 10 in the oblique incidence position having a scattering angle ($\theta$) at which signal intensity is minimum. FIG. 5 graphically shows changes in angles ($\theta$) at which such minimum intensity occurs over a band of frequencies for rectangular shaped voids with two different scattering plane orientations along short and long axes.

Still further, void sizing determination pursuant to the present invention takes into account errors introduced by target material that has an external surface different from the orientation of a flat void surface. The effect on signal measurements of echoes from the void and material external thereto is therefore separated in time within the computer system 38 so that sizing calculations are performed with respect to isolated signals from the void as hereinafter indicated.

Figure 6:
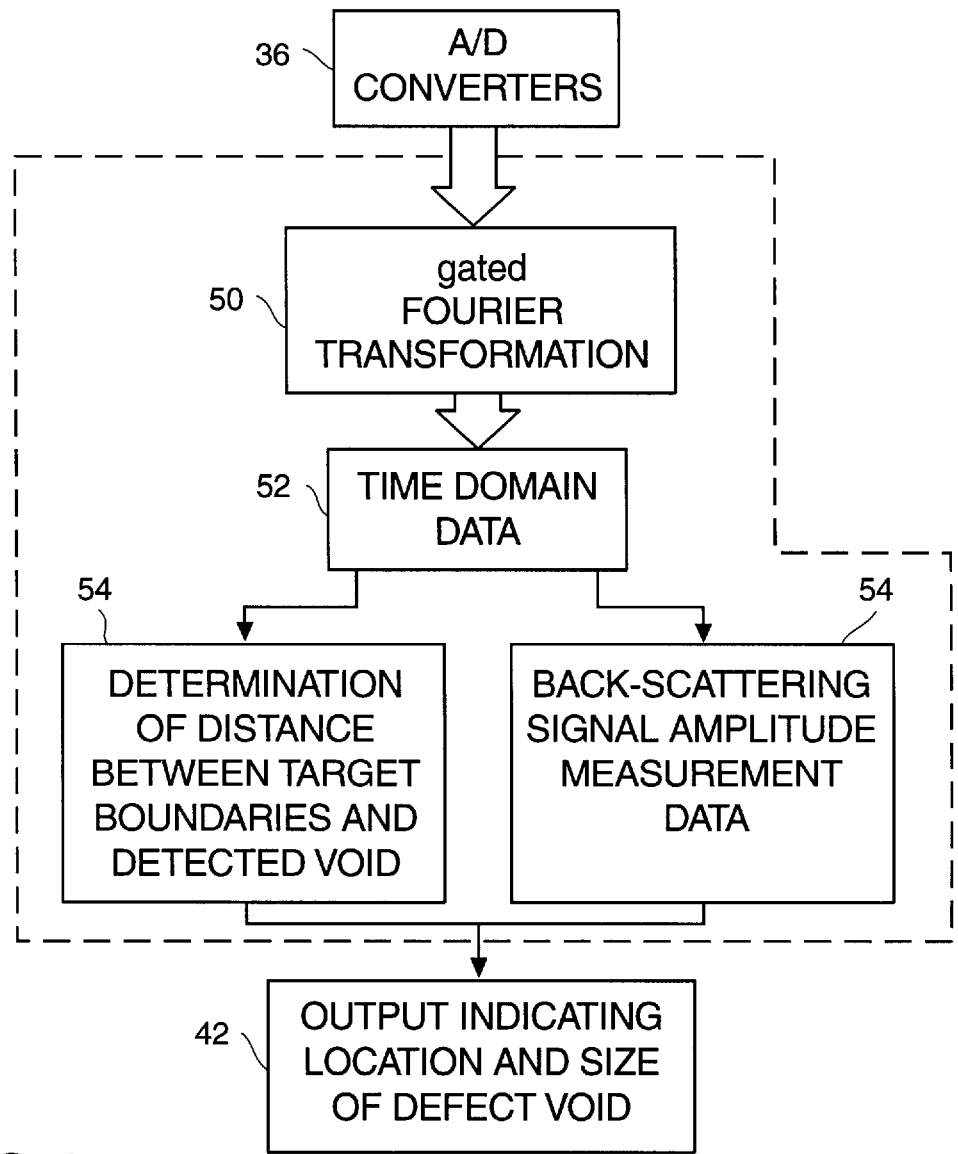
FIG. 6 is a block diagram depicting in greater detail portions of the system diagrammed in FIG. 1.

The foregoing referred to conditions and factors associated with the void defect location and sizing determinations achieved through the computer system 38, is summarized in the program diagram of FIG. 6, tracing the path of calibrated processed data received from network analyzer 34 through digitizer 36 to the output display 42 indicating void location and sizing. The digitized input data undergoes gated Fourier transformation 50 to convert such input signal data from the frequency domain to time domain, denoted by 52 as pulse echo representation of microwave reflection from the defect and surfaces external thereto. From such time domain data, a determination 54 of distance between target boundaries and the detected void is obtained as well as signal amplitude data 56 on the void isolated from the pulse-echo signals. The separated data 54 and 56 form the basis for timely calculating void location and size, to be displayed by output 42, in accordance with the formulae and conditions hereinbefore described.

Figure 7A:
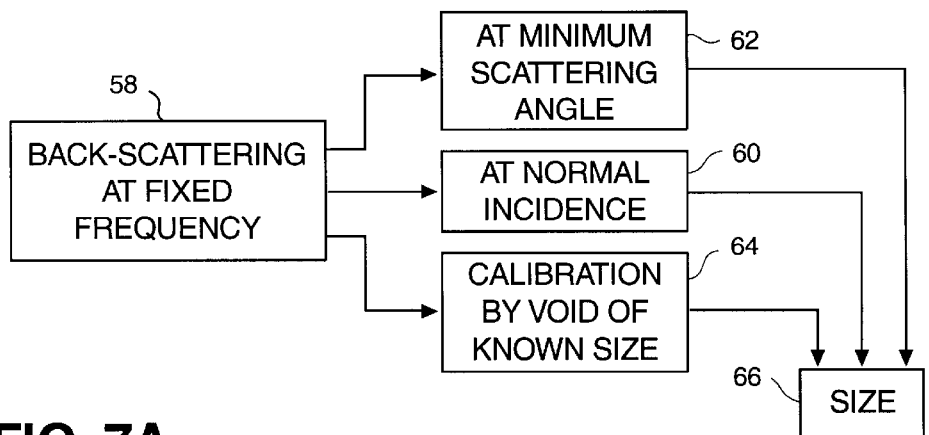
FIGS. 7A and 7B are block diagrams depicting alternative defect size determining methods associated with the present invention.
Figure 7B:
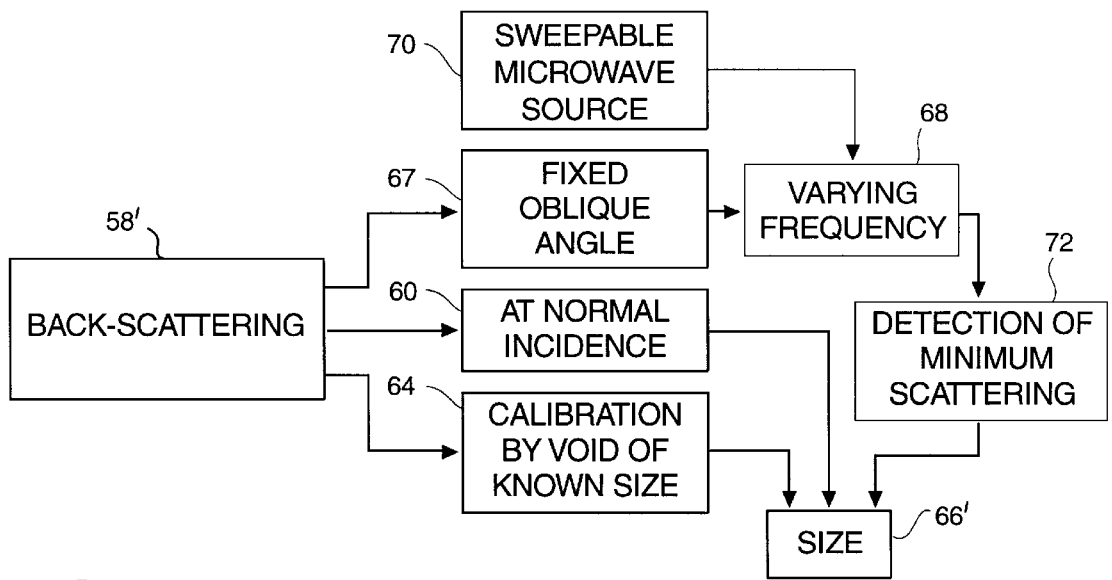

In regard to the method for determination of defect void size pursuant to the present invention, in all cases signal amplitude measurements are obtained through the single antenna 10 in at least two positions consisting of the normal incidence position corresponding to path 12 and the oblique incidence position corresponding to radiation path 18 as hereinbefore described. FIGS. 7A and 7B respectively diagram different variations associated with such defect size determining method.

As diagrammed in FIG. 7A, the signal source 58 is confined to a fixed frequency for the microwave radiation. Measurements of radiation from such source are made with the antenna 10 positioned for normal incidence 60 and for oblique incidence 62 within a range of scattering angles ($\theta$), to search out for that particular scattering angle at which a minimized signal amplitude occurs. Also, a calibration measurement 64 of a void of known size is provided. All three types of measurements 60, 62 and 64 are utilized for size calculation 66 as indicated in FIG. 7A.

According to the size determination method diagrammed in FIG. 7B, the signal source 58' provides measurements 67 made at a fixed oblique angle position of the antenna under a varying frequency 68 imposed from a sweepable frequency microwave source 70. Such measurements 67 are utilized for detection of minimum scattering at one angle ($\theta$) as denoted by 72. Oblique angle measurements so confined to the detected frequency are utilized together with normal incidence measurements 60 and calibration measurements 64 for size calculation 66'.

Obviously, other modifications and variations of the present invention may be possible in light of the foregoing teachings. It is therefore to be understood that within the scope of the appended claims the invention may be practiced otherwise than as specifically described.

What is claimed is:

1. A system for evaluating defects detected within non-metallic material by emission of microwave radiation from a single antenna along a normal incidence path and measurement of microwave radiation reflection, the improvement residing in: adjusting position and orientation of the antenna for also emitting the microwave radiation along at least one oblique incidence path at a selected scattering angle to said normal incidence path at which intensity of the microwave radiation reflection is minimized; and determining location and size of the detected defects from said measurements of the intensities of the microwave radiation reflection along both the normal and oblique incidence paths.

2. The system as defined in claim 1 wherein said step of determining the size of the defect is based on calculating thickness and lateral extent of the defects in the material as function of the measured intensities of the microwave radiation reflection.

3. The system as defined in claim 2 wherein said microwave radiation is emitted from the antenna at a fixed frequency corresponding to calibration data obtained by said step of calculating the thickness and lateral extent with respect to a void of known size in the material.

4. The system as defined in claim 1 wherein said measurements are performed with respect to the emission of the microwave radiation at different frequencies from which lateral extent of the defects are determined by measurements of the intensities of the microwave radiation reflections along oblique incidence paths at different scattering angles.

5. The system as defined in claim 1 wherein said measurements are performed along said one oblique incidence path under varying frequencies of the microwave radiation to detect the minimized intensity for selection of the scattering angle.

6. A system for evaluating defects detected within non-metallic material by emission of microwave radiation from a single antenna along a normal incidence path perpendicular to a targeted surface of said material and measurement of emitted microwave radiation reflection, the improvement residing in: adjusting position and orientation of the antenna for focusing the microwave radiation along at least one oblique incidence path at a selected scattering angle to said normal incidence path at which measured intensity of the microwave radiation reflection is minimized; and determining location of the detected defect in the material from said measurements of the intensities of the reflections along both the normal and oblique incidence paths.

7. The system as defined in claim 6 including the step of calculating size of the detected defects from thickness and lateral extent of voids as functions of the measured intensities of the microwave radiation.

8. A system for evaluating defects detected within non-metallic material by exposure to microwave radiation from a single antenna focused along a normal incidence path perpendicular to a targeted surface of said material and measurement of microwave radiation reflections from the material, the improvement residing in: adjusting position and orientation of the antenna for refocusing the microwave radiation along at least one oblique incidence path at a selected scattering angle to said normal incidence path at which intensity of the microwave radiation reflection is minimized; and determining size of the detected defects from thickness and lateral extent of voids as functions of the intensities of the microwave radiation reflections.

\* \* \* \* \*